US012708304B2

(12) United States Patent
Firoozabadi et al.

(10) Patent No.: US 12,708,304 B2
(45) Date of Patent: Aug. 18, 2026

(54) SYSTEMS AND METHODS FOR VISUAL TRACING OF ABNORMALITY IN DIAGNOSTIC AND MONITORING CLINICAL APPLICATIONS

(71) Applicant: KONINKLIJKE PHILIPS N.V., Eindhoven (NL)

(72) Inventors: Reza Firoozabadi, Thousand Oaks, CA (US); Richard Earl Gregg, Westford, MA (US); Saeed Babaeizadeh, Arlington, MA (US)

(73) Assignee: Koninklijke Philips N.V., Eindhoven (NL)

(*) Notice: Subject to any disclaimer, the term of this patent is extended or adjusted under 35 U.S.C. 154(b) by 506 days.

(21) Appl. No.: 18/115,099

(22) Filed: Feb. 28, 2023

(65) Prior Publication Data

US 2023/0277107 A1 Sep. 7, 2023

Related U.S. Application Data

(60) Provisional application No. 63/315,301, filed on Mar. 1, 2022.

(51) Int. Cl.
*A61B 5/00* (2006.01)
*A61B 5/24* (2021.01)

(52) U.S. Cl.
CPC .............. *A61B 5/24* (2021.01); *A61B 5/0006* (2013.01)

(58) Field of Classification Search
CPC ......... A61B 5/24; A61B 5/0006; A61B 5/339; A61B 5/352; A61B 5/353; A61B 5/355; A61B 5/358; A61B 5/36; A61B 5/366; G16H 40/63; G16H 50/70
See application file for complete search history.

(56) References Cited

U.S. PATENT DOCUMENTS

| | | | | |
|---|---|---|---|---|
| 4,947,857 | A * | 8/1990 | Albert | A61B 5/35 600/509 |
| 5,957,855 | A | 9/1999 | Oriol | |
| 6,741,887 | B1 | 5/2004 | Gleeson | |
| 2010/0228138 | A1 | 9/2010 | Chen | |
| 2011/0021936 | A1* | 1/2011 | Luo | G16H 40/63 345/604 |
| 2012/0083706 | A1 | 4/2012 | Nelwan | |
| 2013/0190637 | A1 | 7/2013 | Zhang | |
| 2014/0125477 | A1 | 5/2014 | Kasuya | |
| 2014/0378856 | A1 | 12/2014 | Koike | |
| 2016/0058318 | A1 | 3/2016 | Borjigin | |
| 2016/0278983 | A1 | 9/2016 | Claus | |
| 2019/0216349 | A1 | 7/2019 | Ji | |
| 2020/0367780 | A1 | 11/2020 | Bardy | |

FOREIGN PATENT DOCUMENTS

| | | | |
|---|---|---|---|
| CN | 110051345 | A | 7/2019 |
| EP | 0448196 | A2 | 9/1991 |

* cited by examiner

*Primary Examiner* — Scott M. Getzow

(57) ABSTRACT

The present disclosure describes various systems and methods of modifying a display to automatically visually trace an abnormality associated with a physiological signal received from a patient (i.e., subject). In particular aspects, the systems and methods described herein utilize three-dimensional display outputs of physiological signals that allow for the immediate differentiation between normal portions of the physiological signal and abnormal portions of the physiological signal.

13 Claims, 12 Drawing Sheets

SYSTEMS AND METHODS FOR VISUAL TRACING OF ABNORMALITY IN DIAGNOSTIC AND MONITORING CLINICAL APPLICATIONS

FIELD OF THE DISCLOSURE

The present disclosure is directed generally to systems and methods of automatically visually tracing an abnormality in a repetitive physiological signal using a three-dimensional visual output.

BACKGROUND

Clinical diagnostic and clinical monitoring applications involve the collection and analysis of repetitive physiological signals. In clinical diagnostic applications, these physiological signals collecting as high-resolution data within a short period of time are used to seek the symptoms of a potential disease, sometimes by inducing a certain situation through exercise or other forms of stress. For example, in a cardiac exercise stress test, having the patient (i.e., subject) walk or run on a treadmill can induce changes in the patient's electrocardiogram heartbeat morphology, which can be collected and measured as a physiological signal. In clinical monitoring application, a long interval of patient physiological signals, such as ECG waveforms, are collected and used either immediately or retrospectively to determine changes to the patient's care. In both diagnostic and monitoring applications, the timing of the abnormal event and the localization of the change in the physiological signal can be critical to providing proper care to the patient.

SUMMARY OF THE DISCLOSURE

The present disclosure is directed generally to automatically visually tracing an abnormality associated with a physiological signal received from a patient or subject.

In one example, a method of automatically visually tracing an abnormality within a physiological signal is provided. The method may comprise: receiving, via one or more sensors, the physiological signal from a subject, wherein the physiological signal is representative of a physiological parameter of the subject over a first period of time; extracting, via at least one processor, a portion-of-interest of the physiological signal, wherein the portion-of-interest of the physiological signal is representative of the physiological parameter of the subject over a second period of time, the second period of time being a subset of the first period of time; determining, via the at least one processor, a signal interval for the portion-of-interest of the physiological signal; determining, via the at least one processor, a plurality of segments of the physiological signal within the portion-of-interest based on the signal interval; determining, via the at least one processor, a potential abnormality within the physiological signal based on the plurality of segments of the physiological signal; generating, via the at least one processor, an output comprising the plurality of segments of the physiological signal within the portion-of-interest and the potential abnormality as a function of time over the second period of time along a first axis and over the signal interval along a second axis; and displaying, on a display, the output.

In an aspect, the physiological signal may comprise electrical signals from the subject's heart, and the physiological parameter comprises heart beats.

In an aspect, the method may further comprise: receiving, via an input device, a user selection identifying the second period of time, wherein the portion-of-interest is determined based on the user selection.

In an aspect, displaying the output may comprise: displaying, on the display, the plurality of segments of the physiological signal within the portion-of-interest and the potential abnormality as a function of time over the second period of time along a first axis and over the signal interval along a second axis; and graphically distinguishing, on the display, the potential abnormality from the plurality of segments of the physiological signal.

In an aspect, the potential abnormality may be graphically distinguished from the plurality of segments of the physiological signal by changing the color of the potential abnormality relative to the plurality of segments of the physiological signal.

In an aspect, the potential abnormality may include at least one of the following: an ST elevation; an ST depression; a prolongation or shortening of the heart rate corrected QT interval; a prolongation or shortening of the QRS duration; a prolongation or shortening of the PR interval; an increased or decreased T-wave amplitude; and a change of P-wave or T-wave shape (monophasic, biphasic, notched).

In an aspect, the display may include an initial representation of the physiological signal, and the method may further comprise: on the display, automatically rearranging the initial representation to display both the initial representation and the generated output.

In an aspect, the initial representation of the physiological signal may include real-time measurements of the physiological signal.

In an aspect, the initial representation of the physiological signal may include measurements of the physiological signal corresponding to at least one of the first period of time and the second period of time.

In an example, another method of automatically visually tracing a potential abnormality within a plurality of physiological signals is provided. The method can comprise: receiving, via a plurality of sensors, the plurality of physiological signals from a subject, wherein the plurality of physiological signals are representative of a physiological parameter of the subject over a first period of time; extracting, via at least one processor, a portion-of-interest of the plurality of physiological signals, wherein the portion-of-interest is representative of the physiological parameter of the subject over a second period of time, the second period of time being a subset of the first period of time; determining, via the at least one processor, a signal interval for the portion-of-interest of the plurality of physiological signals; for each of the plurality of physiological signals within the portion-of-interest, determining, via the at least one processor, a plurality of segments corresponding to at least one of the plurality of physiological signals based on the signal interval; determining, via the at least one processor, a potential abnormality within the plurality of physiological signals based on the plurality of segments corresponding to each of the plurality of physiological signals; generating, via the at least one processor, a plurality of outputs, wherein each output of the plurality of outputs corresponds to an individual physiological signal of the plurality of physiological signals, and wherein each output comprises the plurality of segments that correspond to each individual physiological signal and the potential abnormality as a function of time over the second period of time along a first axis and over the signal interval along a second axis; and displaying, on a display, two or more of the plurality of outputs.

In an aspect, each physiological signal of the plurality of physiological signals may correspond to an individual sensor of the plurality of sensors.

In an aspect, the physiological signal may comprise electrical signals from the subject's heart, and the physiological parameter may comprise heart beats.

In an aspect, the display includes an initial representation of one or more of the plurality of physiological signal, and the method further comprises: on the display, automatically rearranging the initial representation to display both the initial representation and the generated two or more outputs.

In an example, a system for visually tracing an abnormality within a physiological signal is provided. The system can include: a plurality of sensors comprising electrodes and operatively connected to an external power supply; a user interface comprising a display; and a processing unit operatively connected to the plurality of sensors and the user interface. The processing unit may comprise a memory and at least one processor, the memory storing instructions that, when executed by the at least one processor, perform one or more of the following: receive, from the plurality of sensors, a physiological signal from a subject that is representative of a physiological parameter of the subject over a first period of time; extract a portion-of-interest of the physiological signal that is representative of the physiological parameter of the subject over a second period of time, the second period of time being a subset of the first period of time; determine a signal interval for the portion-of-interest of the physiological signal; determine a plurality of segments of the physiological signal within the portion-of-interest based on the signal interval; determine a potential abnormality within the physiological signal based on the plurality of segments of the physiological signal; generate an output comprising the plurality of segments of the physiological signal within the portion-of-interest and the potential abnormality as a function of time over the second period of time along a first axis and over the signal interval along a second axis; and display, on the display of the user interface, the output.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

The present disclosure describes various systems and methods of modifying a display to automatically visually trace an abnormality associated with a repetitive physiological signal received from a patient (i.e., subject). Specifically, the systems and methods of detecting and visually tracing abnormalities within a physiological signal (e.g., ECG waveforms) are directed to improving clinical diagnostic and monitoring apparatuses and techniques where complicated and numerous physiological signals must be processed and analyzed by a computer before being displayed on a user interface. The physiological signals as discussed herein are repetitive and/or periodic signals with repeating cycles that can be compared over time. In particular aspects, the systems and methods described herein utilize three-dimensional display outputs of physiological signals that allow for the immediate differentiation between normal portions of the physiological signal and abnormal portions of the physiological signal. In further aspects, the existing display comprising other waveforms, measurements, plots, and option menus can be modified to enable the optional and/or simultaneous display of the generated outputs. In still further aspects, the physiological parameter being measured is heartbeats/pulses, and the physiological signal includes the electrical signals associated with the heart.

Figure 1:
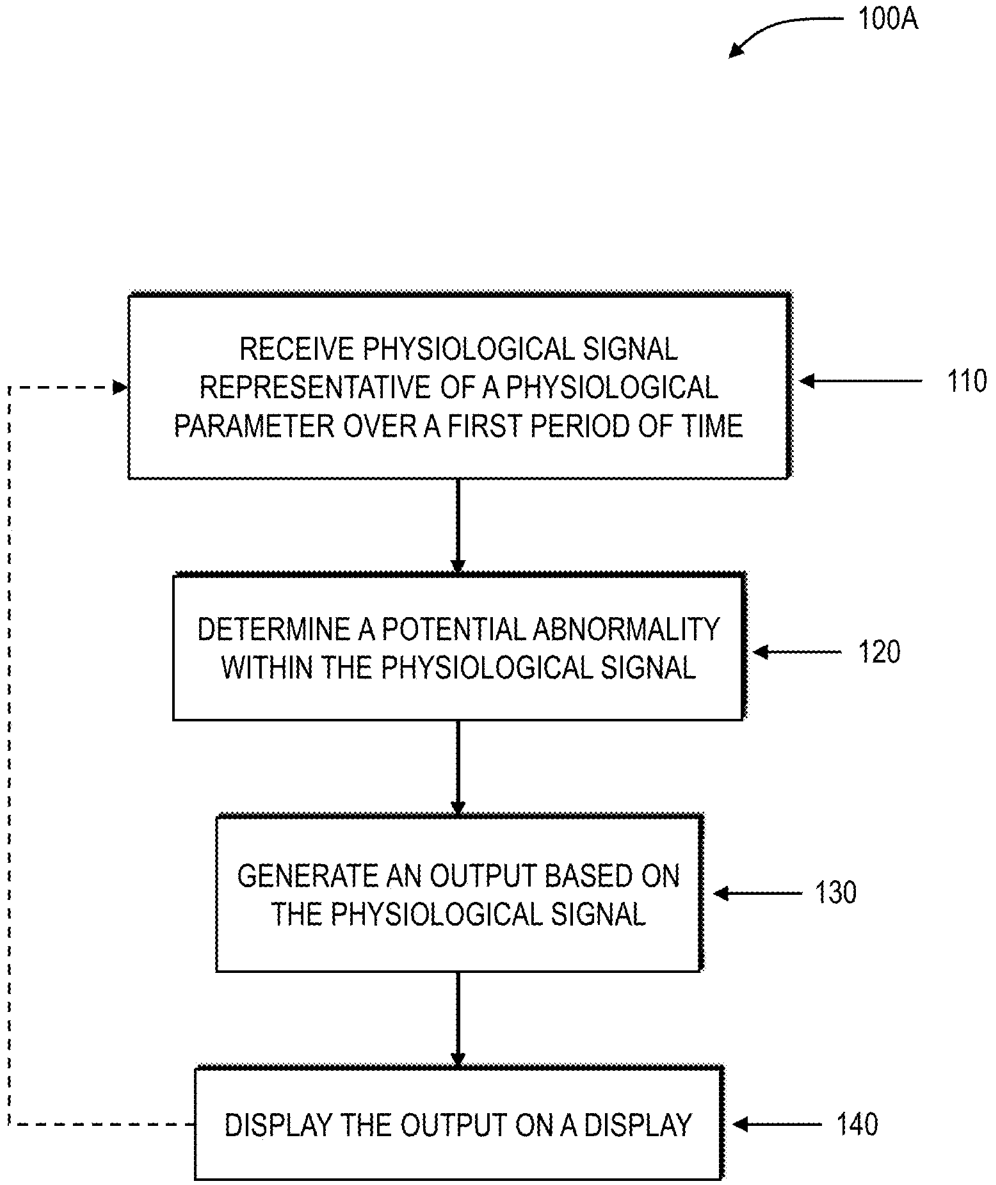
FIG. 1 is a flowchart illustrating a method of visually tracing an abnormality within a physiological signal according to an aspect of the present disclosure.
Figure 2:
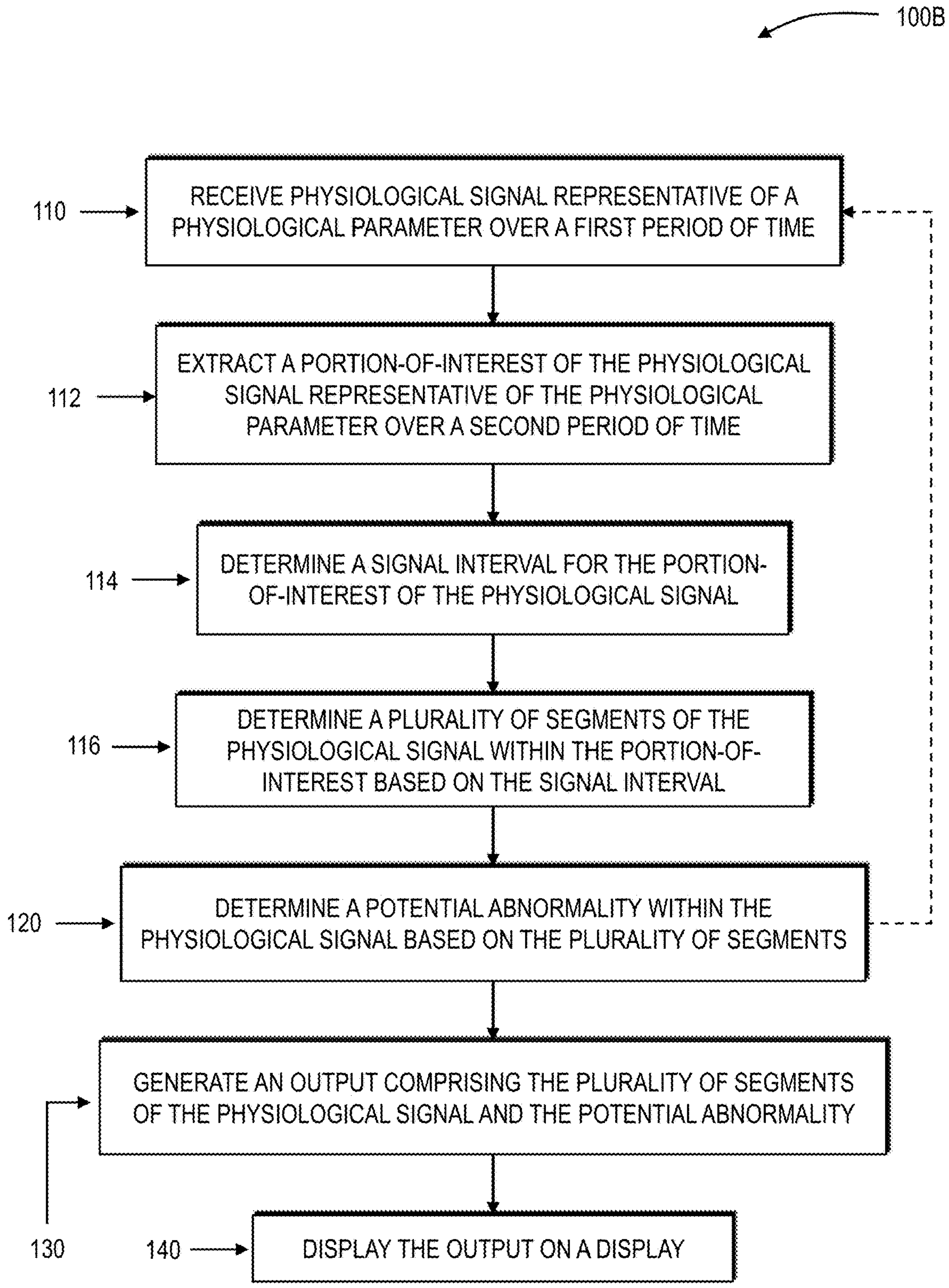
FIG. 2 is a flowchart illustrating a method of visually tracing an abnormality within a physiological signal according to another aspect of the present disclosure.
Figure 3:
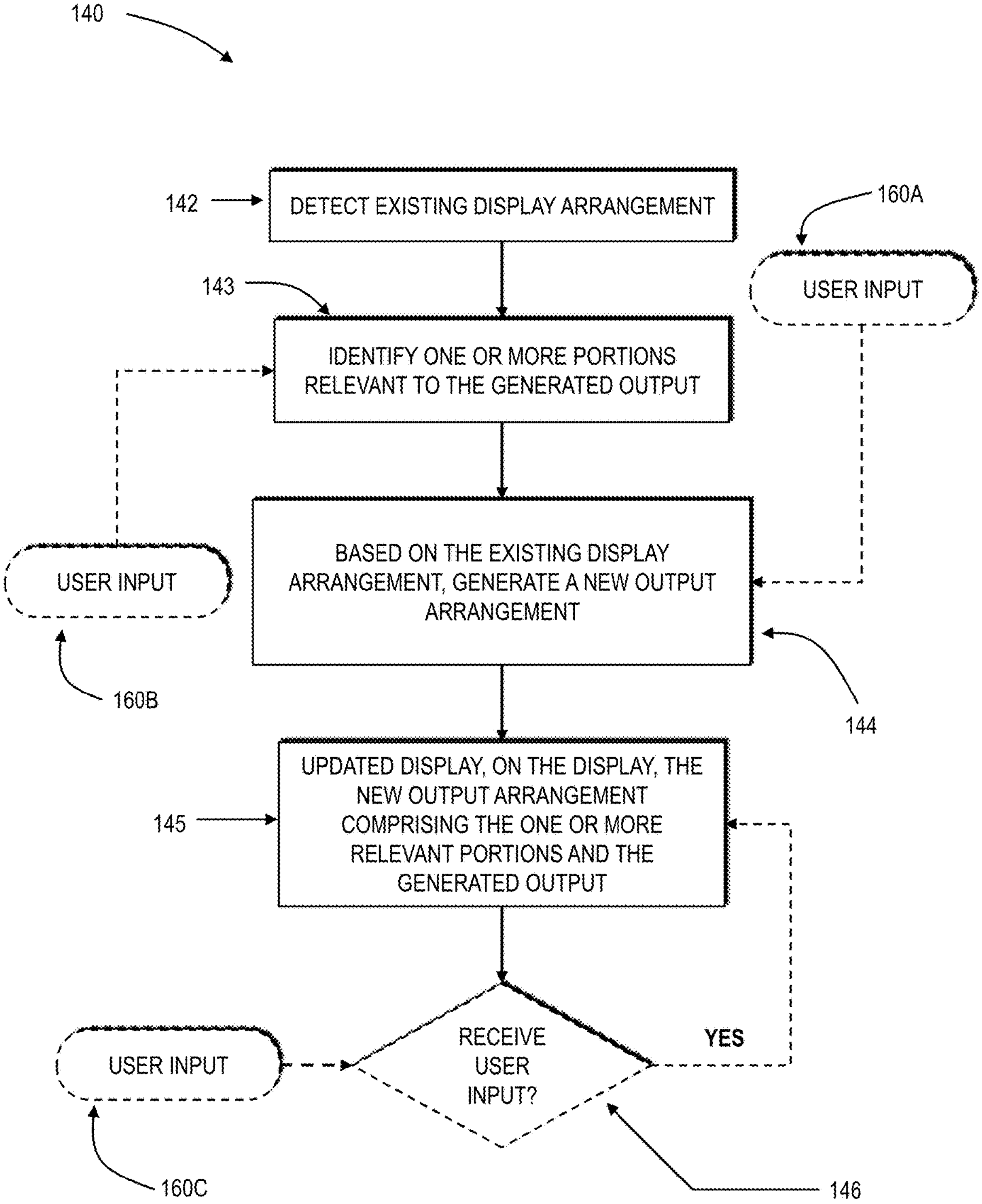
FIG. 3 is a flowchart illustrating a method of visually tracing an abnormality within a physiological signal according to still further aspects of the present disclosure.

With reference to FIGS. 1-3, these and other aspects of the methods 100A, 100B for modifying a display to automatically visually trace an abnormality associated with a physiological signal received from a patient are described. Turning to FIG. 1, a method 100A for modifying a display to automatically visually trace an abnormality associated with a physiological signal is shown in accordance with certain aspects of the present disclosure.

At a step 110, the method 100A comprises receiving a physiological signal that is representative of a physiological parameter over a first period of time. In an aspect, the physiological signal is received from a patient (i.e., subject) using one or more sensors, including a plurality of sensors. In particular aspects, the physiological signal can be electrical signals associated with the patient's heartbeat, and the physiological parameter can be the patient's heartbeat/heart function. In further aspects, the physiological signal can be collected over a first period of time. In clinical diagnostic applications, the first period of time can include a testing period or a portion thereof. For example, the physiological signal can be collected over a first period of time that includes a cardiovascular stress test, such while a patient is running on a treadmill. In specific aspects, the first period of time can be at least about 5 minutes, including at least about 10 minutes, at least about 15 minutes, at least about 20 minutes, at least about 30 minutes, and ranges having any combination of endpoints thereof.

At a step 120, the method 100A comprises determining a potential abnormality within the physiological signal received from the one or more sensors over the first period of time. In certain aspects, the physiological signal can be an ECG and the potential abnormality can be at least one of: an ST elevation; an ST depression; a prolongation or shortening of the heart rate corrected QT interval; a prolongation or shortening of the QRS duration; a prolongation or shortening of the PR interval; an increased or decreased T-wave amplitude; and a change of P-wave or T-wave shape (monophasic, biphasic, notched). More specifically, the potential abnormality can include a change in QRS duration or the T-wave due to immediate and/or near-term developments in heart function, such as faster changes in myocardial ischemia (over minutes or hours), or can include changes in Q, R, S, and T-waves due to longer-term phenomena like evolving myocardial infarction (over the course of days to weeks).

At a step 130, the method 100A comprises generating an output based on the physiological signal. In an aspect, the output generated comprises the physiological signal or a portion thereof and, if identified, the potential abnormality. In further aspects, the output can include be one or more three-dimensional representations of the physiological signal (or portions thereof) as a function of time, wherein a first axis of the output represents one period of time and a second axis of the output represents another period of time. In still further aspects, the output can graphically distinguish the potential abnormality from other portions of the physiological signal within the output.

At a step 140, the method 100A comprises displaying the generated output on a display. In certain aspects, the display can already include an initial output that is representative of the physiological signal and/or other patient-related information. For example, the initial output can include real-time measurements of the physiological signal. Accordingly, the step 150 can include automatically rearranging the initial output on the display in order to display both the initial output and the generated three-dimensional output.

Turning to FIG. 2, these and other aspects of the method of the present disclosure are described. As illustrated, a method 100B for modifying a display to automatically visually trace an abnormality associated with a physiological signal is provided. At a step 110, the method 100B comprises receiving a physiological signal over a first period of time, as described above.

At a step 112, the method 100B can include extracting a portion-of-interest from the physiological signal that is representative of the physiological parameter over a second period of time. In an aspect, the second period of time is different than the first period of time. For example, the second period of time can be a subset of the first period of time. The second period of time can represent a particular period of interest, such as a period of heightened physical activity for the patient. In specific aspects, the second period of time can be from about 5 minutes to about 30 minutes. In additional aspects, step 112 can further include receiving, via an input device, a user selection identifying the second period of time; and extracting the portion-of-interest based on the user selection.

At a step 114, the method 100B can include determining a signal interval for the portion-of-interest of the physiological signal. In particular aspects, the signal interval can be a period of time representing one heartbeat/pulse. In further aspects, the signal interval can be a predetermined offset value that is then used to determine or extract a plurality of segments from the physiological signal. In an aspect, the signal interval is a predetermined offset value that is determined based on the period of the physiological signal (e.g., the subject's heart rate) or based on a predetermined percentage of the cycle time of the physiological signal. For example, where the physiological signal comprises a subject's heart beats, the signal interval can be a percentage of the cycle time (based on the heart rate or RR interval) between at least a first alignment point and at least a second alignment point.

At a step 116, the method 100B can include determining a plurality of segments of the physiological signal within the portion-of-interest based on the signal interval. In an aspect, each segment of the plurality of segments can be the physiological signal representative of a single heartbeat/pulse. In other words, representative portions of the physiological signal (e.g., ECG, etc.) within the portion-of-interest are extracted based on the signal interval.

In particular aspects, the method 100B includes a step of determining a plurality of alignment points within the portion-of-interest, and the step 116 of determining a plurality of segments includes extracting a segment around each of the plurality of alignment points based on the signal interval. As such, each segment of the plurality of segments can begin at a fixed offset preceding the corresponding alignment point and can end at a fixed offset following the corresponding alignment point.

In further aspects, each segment of the determined plurality of segments may include one or more cycles of the physiological signal, including two or more cycles of the physiological signal. For example, each segment can include two or more heart beats.

At a step 120, the method 100B comprises determining a potential abnormality within the physiological signal, as described above. In further aspects, the potential abnormality may be determined based on at least the plurality of segments.

At a step 130, the method 100B comprises generating an output, as discussed above. In further aspects, the output can comprise the plurality of segments of the physiological signal and the potential abnormality.

At a step 140, the method 100B comprises displaying, on a display, the generated output, as described above.

Turning to FIG. 3, additional aspects of step 140 are described. In particular the step 150 of displaying, on the display, the generated output can include: detecting an existing display arrangement (step 142); identifying one or more portions of the existing display arrangement that are relevant to the generated output (step 143); generating a new output arrangement based on the existing arrangement, wherein the new output arrangement includes the one or more relevant portions of the existing display arrangement as well as the generated output (step 144); and updating the display to display the new output arrangement (step 145).

In certain aspects, user input 160A, 160B, 160C can optionally be received at certain points in the methods 100A, 100B, as shown in FIG. 3. In some aspects, the steps 143, 144 can be performed based on user input 160A, 160B. In further aspects, when displaying the generated output, the methods 100A, 100B can include a step 146 that enables one or more of the three-dimensional representations of the generated output to be displayed, either individually or together, simultaneously, in a rotation, or on-demand.

Figure 4:
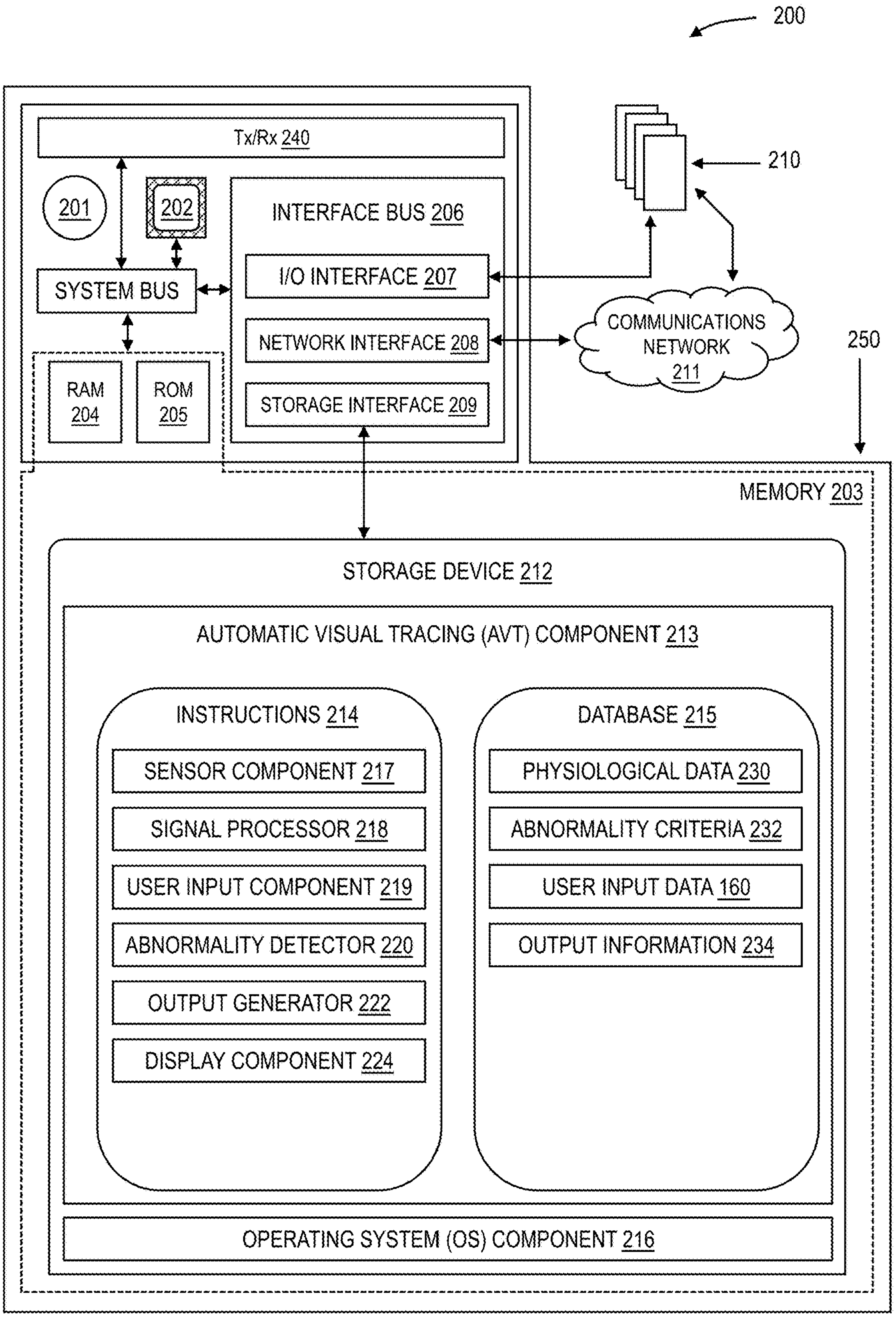
FIG. 4 is a block diagram of a system for automatically visually tracing an abnormality within a physiological signal according to an aspect of the present disclosure.
Figure 5:
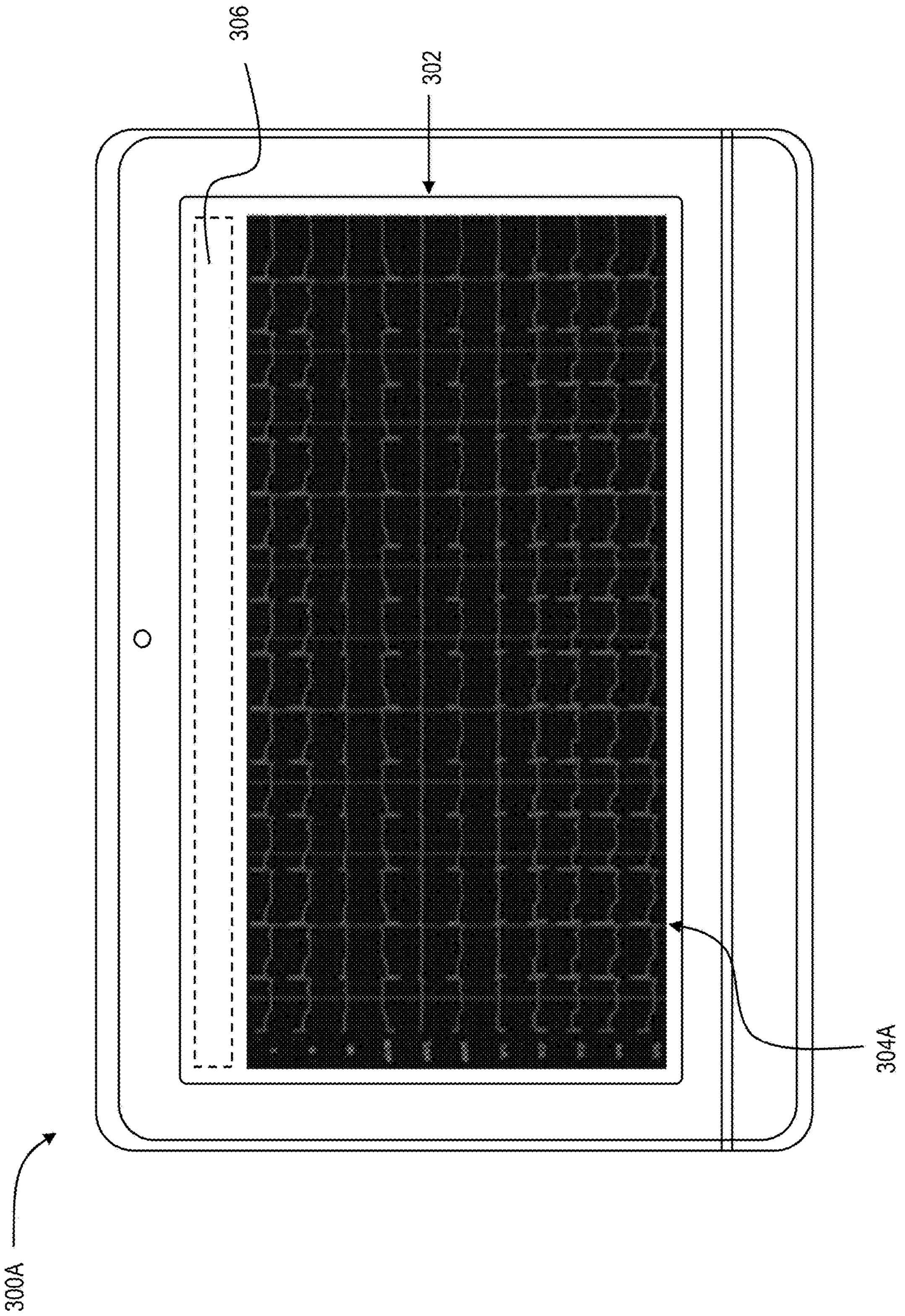
FIG. 5 illustrates a first display used for automatically visually tracing an abnormality within a physiological signal according to various aspects of the present disclosure.

Turning now to FIG. 4, a block diagram of a system 200 comprising an automatic visual tracing (AVT) controller 250 is illustrated in accordance with certain aspects of the present disclosure. In certain aspects, the AVT controller 250 can serve to perform one or more steps of the methods described above. As shown, system 200 can include one or more external/peripheral devices 210 and/or communication networks 211 that are operatively connected to the AVT controller 250. That is, the AVT controller 250 can be connected to and/or communicate with one or more peripheral devices 210 and/or a communications network 211 (e.g., local area networks, wide area networks, wireless local area networks, etc.). In particular aspects, the peripheral devices 210 include one or more user interfaces or displays. For example, the peripheral devices 210 can include: graphics tablets; joysticks; keyboards; microphones; computer mouse (mice); touch screens (e.g., capacitive, resistive, etc.); trackballs; trackpads; styluses; audio devices; cameras; printers; video devices; and/or the like. According to the present disclosure, the peripheral devices 210 include one or more sensors that are used to measure a physiological signal associated with a subject, as described above. In specific embodiments, the one or more sensors can include electrodes and/or be connected to an external power supply.

According to the present disclosure, the AVT controller 250 can comprise one or more processors 202 operatively connected to a memory 203 that store instructions 214 for performing one or more of the steps of the methods described herein. The memory 203 can include one or more forms of transitory and/or non-transitory memory, including random access memory 204, read only memory 805, and storage device 212. The AVT controller 250 can include an interface bus 206 can include one or more components that facilitates communication with the peripheral devices 210 and/or communication networks 211, including, but not limited to, an input/output (I/O) interface 207, a network interface 208, and and/or a storage interface 209. The components of the AVT controller 250 can be interconnected and communicate via a system bus 216. The AVT controller 250 can include an internal power source 201 and/or be connected to an external power source. The AVT controller 250 can further include transceivers that facilitate wireless communication, including wireless communication between the controller 250 and one or more of the peripheral devices 210.

The memory 203 of the AVT controller 250 can contain a collection of program and/or database components and/or data such as, but not limited to: operating system component (s) 236 (operating system); sensor component(s) 217; signal processing component(s) 218; user input component(s) 219; abnormality detection component(s) 220; output generator component(s) 222; and/or display component(s) 224. These components may be stored and accessed from the storage device(s) 212 accessible through the interface bus 206. In certain aspects, one or more of the components are stored in a local storage device 212. Alternatively, one or more of these components can also be loaded and/or stored in memory 203 via certain peripheral devices, external memory devices, remote storage devices, and the like.

In an aspect, the sensor component 217 can be a stored program component that, when executed by at least one processor 202, receives different physiological signals from one or more sensors (e.g., peripheral devices 210) and stored the physiological signals in the database 215 of the storage device 212 as physiological data 230.

In an aspect, the signal processing component 218 can be a stored program component that, when executed by at least one processor 202, processes and analyzes the physiological data 230.

In an aspect, the user input component 219 can be a stored program component that, when executed by at least one processor 202, receives user input (e.g., 160A, 160B, 160C, etc.) from one or more peripheral devices 210 and stored the input as user input data 160.

In an aspect, the abnormality detection component 220 can be a stored program component that, when executed by at least one processor 202, determines/identifies an abnormality or potential abnormality within the physiological data 230. In particular, the abnormality detection component 220 can, when executed by at least one processor 202, perform one or more of the following: extract a portion-of-interest of the physiological signal that is representative of a physiological parameter of the subject over a period of time; determine a signal interval for the portion-of-interest of the physiological signal; determine a plurality of segments of the physiological signal within the portion-of-interest based on the signal interval; and/or determine a potential abnormality within the physiological signal based on the plurality of segments of the physiological signal. In certain aspects, the potential abnormality within the physiological signal can be determined based on a pre-determined set of rules, such as abnormality criteria 232, the define when a particular physiological signal or a trend in the physiological signal is abnormal for the subject.

In an aspect, the output generator component 222 can be a stored program component that, when executed by at least one processor 202, generates an output comprising one or more representations of the physiological signal over a period of time, which may be stored as output information 234. In particular aspects, the one or more representations can be one or more three-dimensional representations of the physiological signal over a period of time. In further aspects, each representation of the output can include a plurality of segments of the physiological signal within a portion-of-interest and a potential abnormality as a function of time over one period of time along a first axis and over a signal interval (e.g., duration) along a second axis. In still further aspects, the output can provide the output information 234 such that the potential abnormality or abnormalities can be graphically distinguishing from the rest of the plurality of segments of the physiological signal.

In an aspect, the display component 224 can be a stored program component that, when executed by at least one processor 202, displays the output information 234 (or a portion thereof) on an associated display. In certain aspects, the display component 224 can, when executed by at least one processor 202, graphically distinguish the determined abnormalities from the plurality of segments of the physiological signal by changing the color of the potential abnormality on the display relative to the plurality of segments of the physiological signal. In further aspects, the display component 224 can process the signal in order to graphically distinguish the determined abnormalities from the remainder of the plurality of segments by emphasizing and/or de-emphasizing various aspects of the physiological signal. For example, the amplitudes of a portion of the plurality of segments may be enhanced or compressed for emphasis, and the time scale corresponding to the signal interview and/or measurement period may be contracted and/or expanded for emphasis. More specifically, the display component 224 can, when executed by the at least one processor 202, generate a three-dimensional representation of the physiological signal that graphically distinguishes the determined abnormalities from the rest of the plurality of segments of the physiological signal by at least one of the following: enhancing the amplitude of a portion of the physiological signal; compressing the amplitude of a portion of the physiological signal; contracting a time scale associated with the physiological signal; and expanding a time scale associated with the physiological signal.

In further aspects, the display component 224 can, when executed by at least one processor 202, perform one or more of the following: detect an existing display arrangement including patient information (e.g., the physiological signal and/or information related to the physiological signal); identify one or more portions of the existing display arrangement that are relevant to the output generated by the output component 222; generate a new output arrangement comprising the one or more relevant portions of the existing display arrangement as well as the generated output; update the display to display the new output arrangement; and, optionally, update the display based on user input that is received as discussed above.

Turning now to FIGS. 5-12, further aspects of the displays and user interfaces are described.

Figure 6:
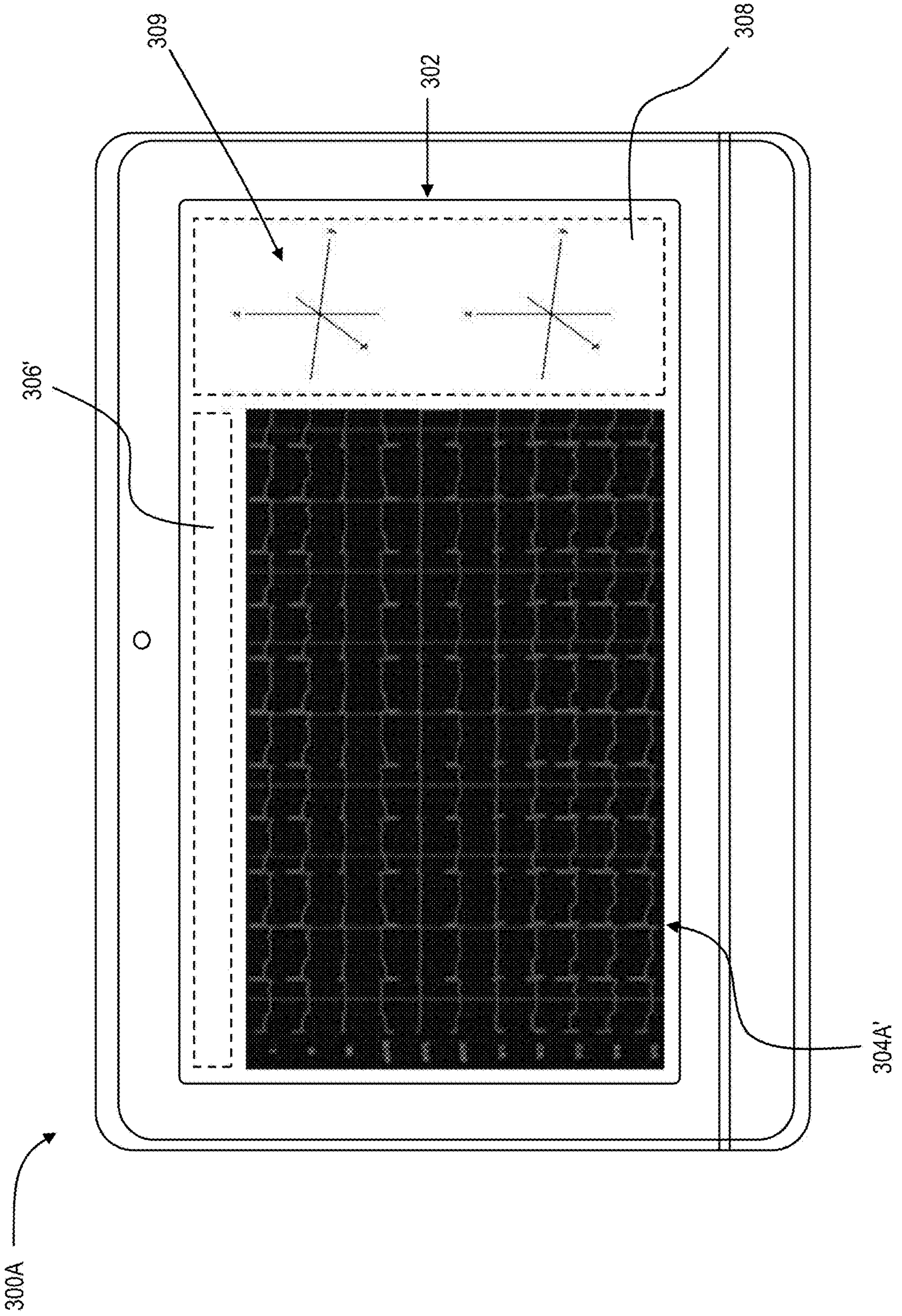
FIG. 6 illustrates a display and a first display arrangement used for automatically visually tracing an abnormality within a physiological signal according to various aspects of the present disclosure.
Figure 7:
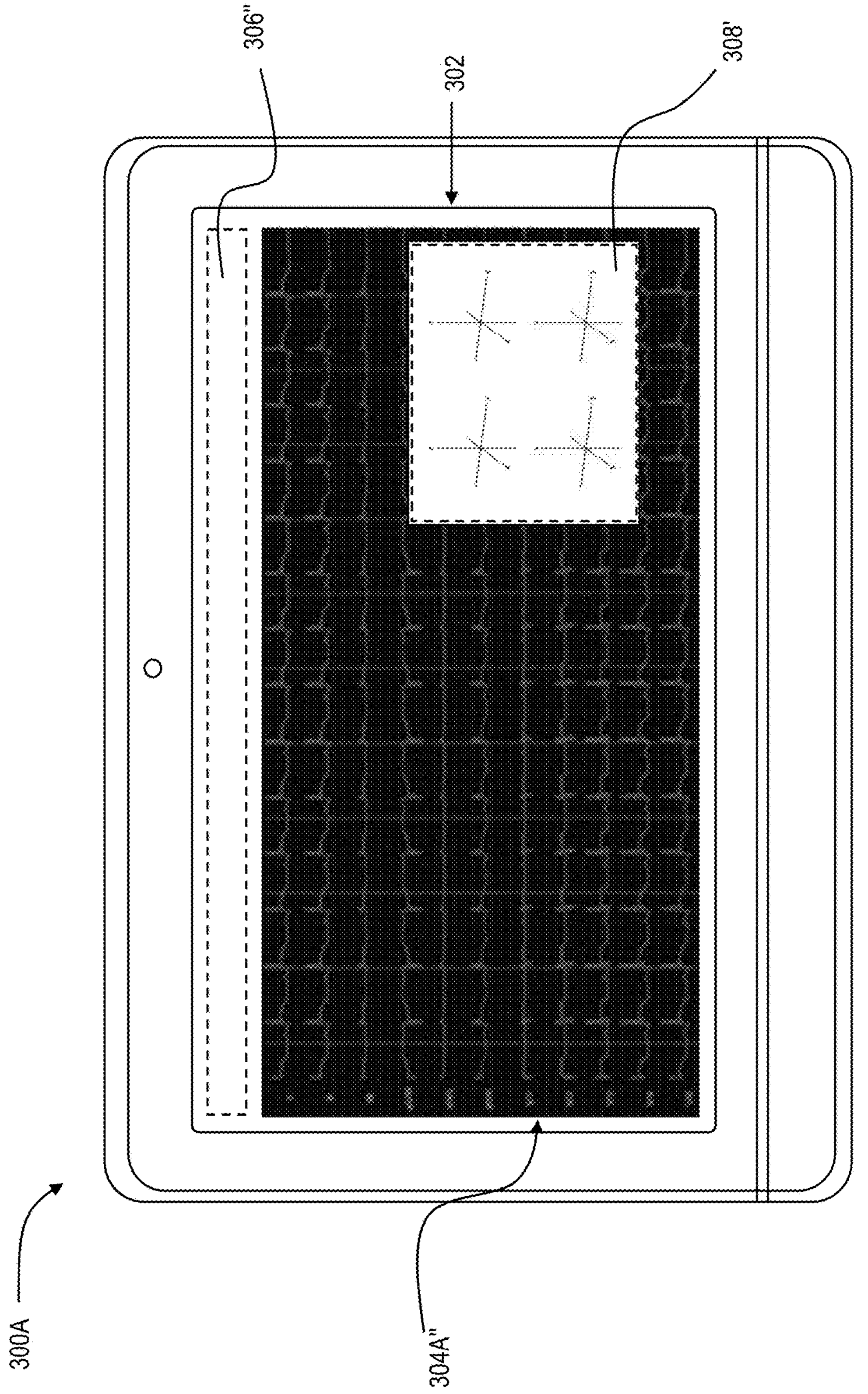
FIG. 7 illustrates a display and a second display arrangement used for automatically visually tracing an abnormality within a physiological signal according to various aspects of the present disclosure.

With reference to FIGS. 5-9, a user interface 300A is illustrated. In some aspects, the user interface 300A can include the AVT controller 250 or be a device connected to the AVT controller 250 (e.g., a peripheral device 210). The user interface 300A can include a display 302 with an existing display arrangement including physiological signals 304A and menu options 306. As shown, the physiological signals 304A can include signals from one or more sensors, which may be relevant to the generated output. As shown in FIG. 6, the display 302 is modified and updated to include a new arrangement of physiological information 304A', a new menu arrangement 306', and the output 308 comprising one or more new representations 309 of the physiological information. As shown in FIG. 7, the display arrangement can be modified in alternative configurations, such as using a floating window 308' overlapping a portion of the existing physiological signal display 304A".

Figure 8:
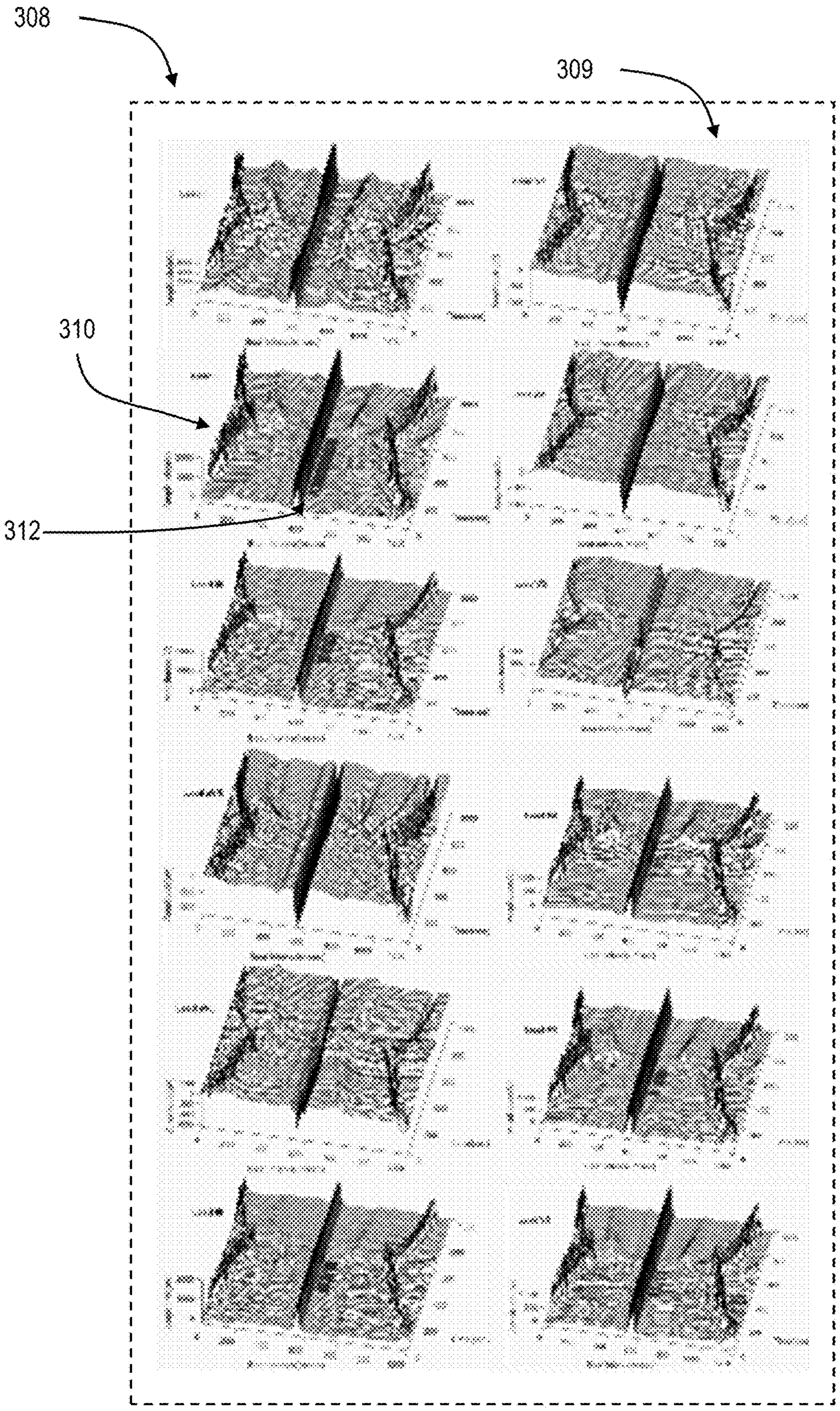
FIG. 8 illustrates a display arrangement used for automatically visually tracing an abnormality within a physiological signal according to various aspects of the present disclosure.
Figure 9:
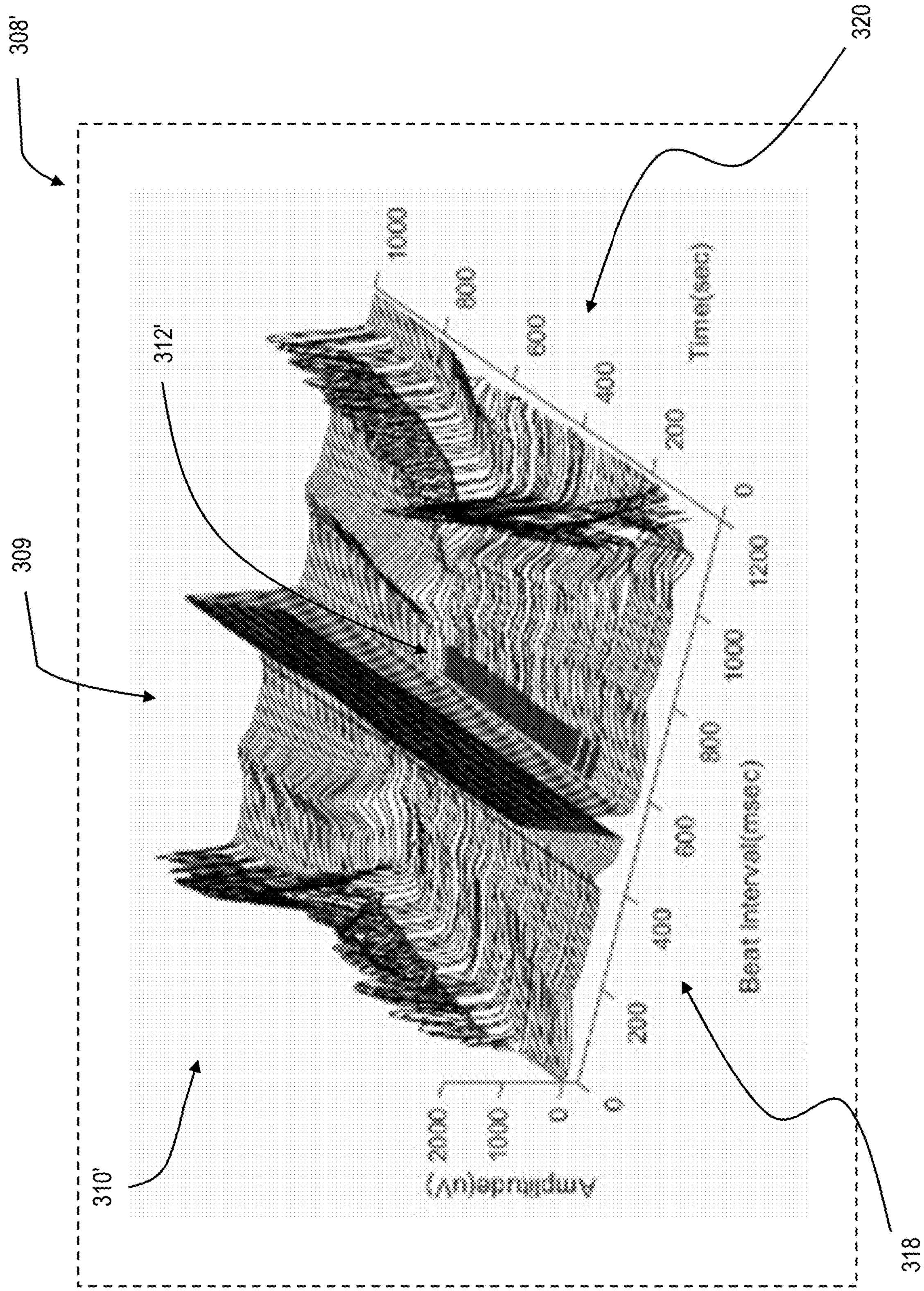
FIG. 9 illustrates another display arrangement used for automatically visually tracing an abnormality within a physiological signal according to various aspects of the present disclosure.
Figure 10:
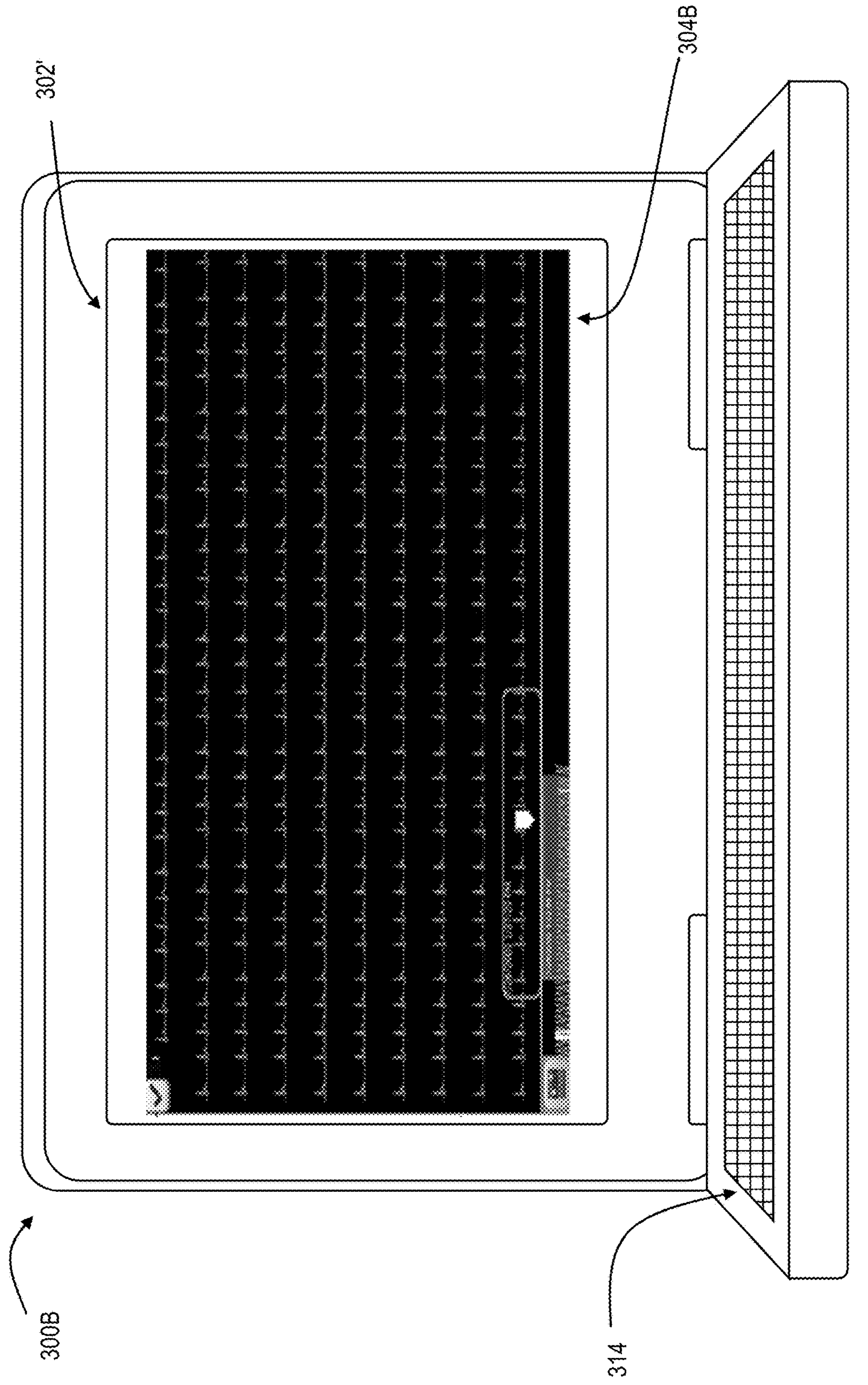
FIG. 10 illustrates a second display used for automatically visually tracing an abnormality within a physiological signal according to various aspects of the present disclosure.

As shown in FIGS. 8 and 9, the outputs 308, 308' can include one or more three-dimensional representations 309 of the physiological signal (or portions thereof). According to the present disclosure, one or more of such representations 309 of the output 308, 308' can include portions of the physiological signal 310 and one or more potential abnormalities 312 that are graphically distinguished from one another. In certain aspects, the output 308' includes only one three-dimensional representation 309 at a time, as shown in FIG. 9. In particular aspects, the three-dimensional representations 309 can include a plurality of segments 310' of the physiological signal and the potential abnormality 312' arranged on a plot having a first axis 318 that is a signal interval/duration associated with the plurality of segments 310' and a second axis 320 that is a monitoring and/or diagnostic period of time. In other words, the output comprises the plurality of segments 310' of the physiological signal within a portion-of-interest and the potential abnormality as a function of time over a signal interval along a first axis 318 and over a period of time along a second axis 320.

As described herein, the three-dimensional representations 309 can include a plurality of segments 310' of the physiological signal and the potential abnormality 312' that are arranged on a plot having a first axis 318 and a second axis 320, wherein each segment is aligned on the plot based on a plurality of alignment points. As shown in FIG. 9 (and also in FIG. 12), the plurality of alignment points are the R-wave peaks of the physiological signal and the plurality of segments 310' are aligned on the first axis 318 based on the signal interval around the plurality of alignment points. Further, as shown in FIG. 9 (And also in FIG. 12), the signal interval for the plurality of segments 310' may be set for the entire physiological signal within the portion-of-interest, and therefore the segments 310' can include overlapping portions at the beginning and/or end of each segment 310'.

According to further aspects of the present disclosure, another user interface 300B is provided having a different display arrangement 302' showing one or more aspects of the physiological signal 304B. As discussed above, the user interface 300B can include the AVT controller 250 or be a device connected to the AVT controller 250 (e.g., a peripheral device 210). In certain aspects, the user interface 300B can include and/or be connected with a user input device 314 that can receive input (e.g., input 160A, 160B, 160C, etc.) from an associated user.

Figure 11:
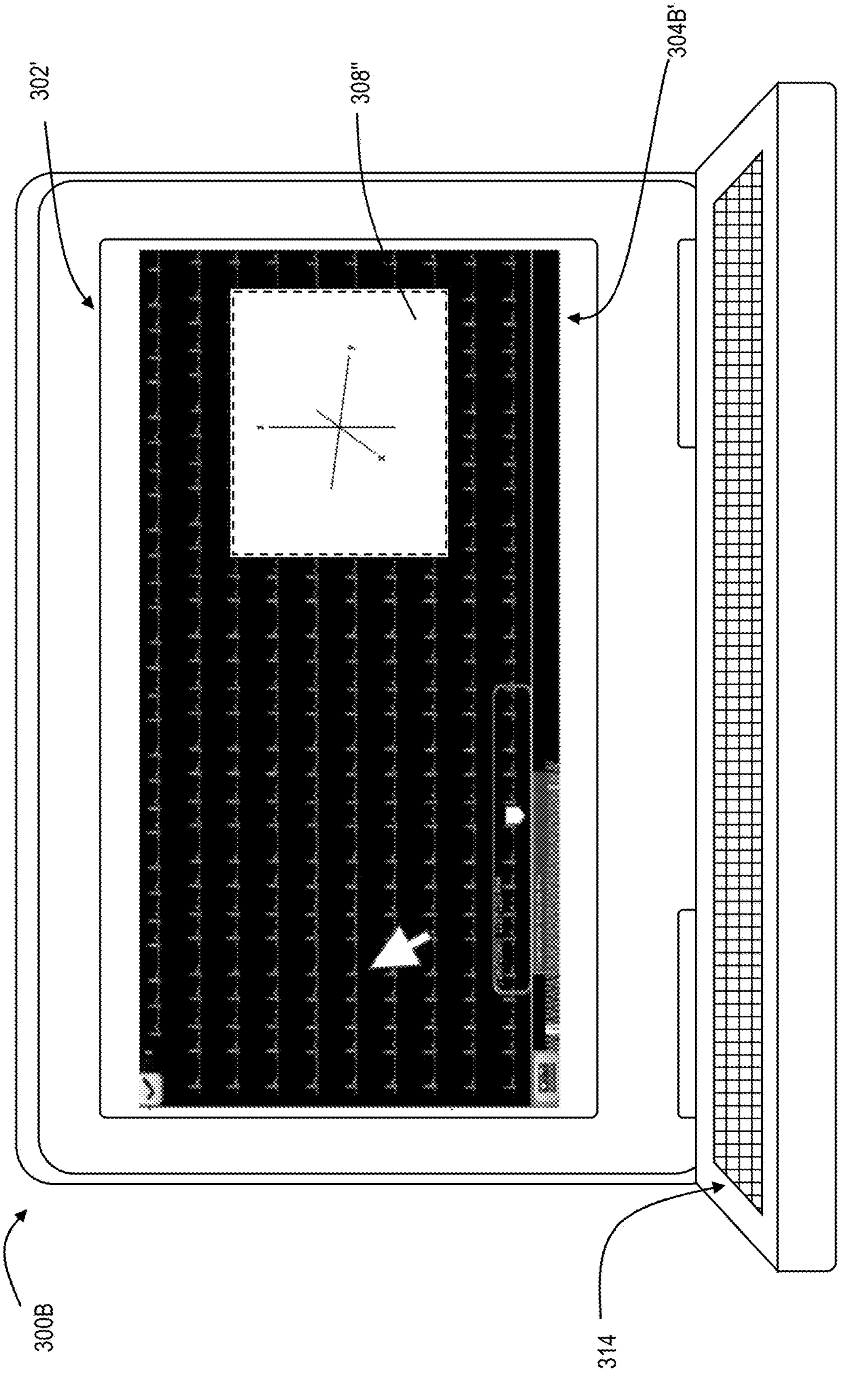
FIG. 11 illustrates a display and third display arrangement used for automatically visually tracing an abnormality within a physiological signal according to various aspects of the present disclosure
Figure 12:
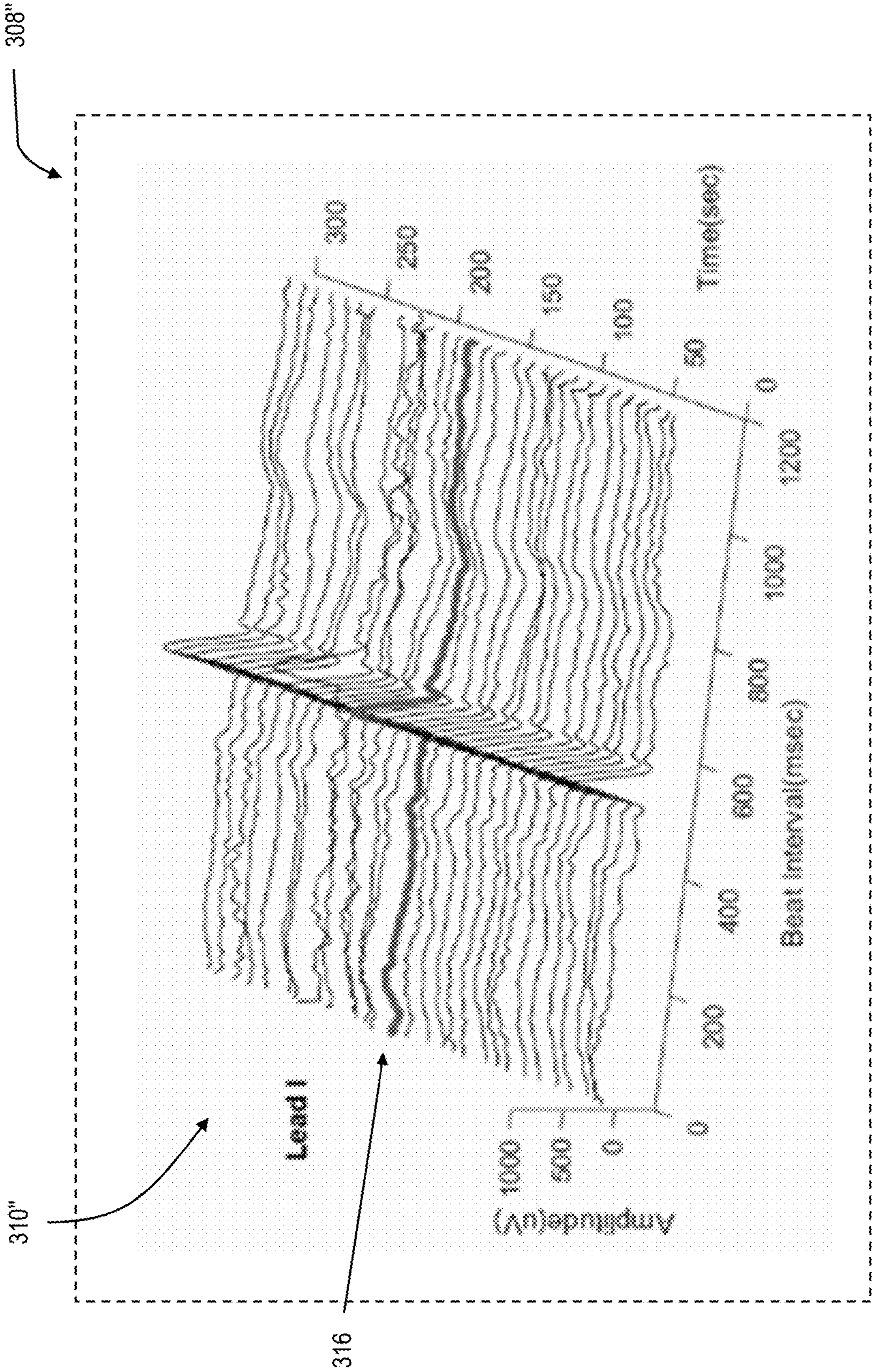
FIG. 12 illustrates a fourth display arrangement used for automatically visually tracing an abnormality within a physiological signal according to various aspects of the present disclosure

As shown in FIG. 11, the associated user can provide input via the user input device 314 to select one or more of the physiological signals displayed on the display 304B, which directs the AVT controller 250 to update the display 302' to include a generated output 308" corresponding to the selected signal(s). As discussed above, the generated output 308" can include a three-dimensional representation of the physiological signal. However, as shown in FIG. 12, the generated output 308" can also graphically distinguish a single segment 316 of the plurality of segments 310" of the physiological signal.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

All definitions, as defined and used herein, should be understood to control over dictionary definitions, definitions in documents incorporated by reference, and/or ordinary meanings of the defined terms.

The indefinite articles “a” and “an,” as used herein in the specification and in the claims, unless clearly indicated to the contrary, should be understood to mean “at least one.”

The phrase “and/or,” as used herein in the specification and in the claims, should be understood to mean “either or both” of the elements so conjoined, i.e., elements that are conjunctively present in some cases and disjunctively present in other cases. Multiple elements listed with “and/or” should be construed in the same fashion, i.e., “one or more” of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

It should also be understood that, unless clearly indicated to the contrary, in any methods claimed herein that include more than one step or act, the order of the steps or acts of the method is not necessarily limited to the order in which the steps or acts of the method are recited.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method of automatically visually tracing an abnormality within a physiological signal, the method comprising:

receiving, via one or more sensors, the physiological signal from a subject, wherein the physiological signal is representative of a physiological parameter of the subject over a first period of time;

extracting, via at least one processor, a portion-of-interest of the physiological signal, wherein the portion-of-interest of the physiological signal is representative of the physiological parameter of the subject over a second period of time, the second period of time being a subset of the first period of time;

determining, via the at least one processor, a signal interval for the portion-of-interest of the physiological signal;

determining, via the at least one processor, a plurality of segments of the physiological signal within the portion-of-interest based on the signal interval;

determining, via the at least one processor, a potential abnormality within the physiological signal based on the plurality of segments of the physiological signal;

generating, via the at least one processor, a three-dimensional visual output (309) comprising the plurality of segments of the physiological signal within the portion-of-interest and the potential abnormality as a function of time over the second period of time along a first axis and over the signal interval along a second axis; and displaying, on a display, the three-dimensional visual output, wherein the display includes an initial representation of the physiological signal, and the method further comprises:

on the display, automatically rearranging the initial representation to display both the initial representation and the generated output.

2. The method of claim 1, wherein the physiological signal comprises electrical signals from the subject's heart, and the physiological parameter comprises heart beats.

3. The method of claim 2, wherein the potential abnormality includes at least one of the following: an ST elevation; an ST depression; a prolongation or shortening of the heart rate corrected QT interval; a prolongation or shortening of the QRS duration; a prolongation or shortening of the PR interval; an increased or decreased T-wave amplitude; and a change of P-wave or T-wave shape.

4. The method of claim 1, further comprising:

receiving, via an input device, a user selection identifying the second period of time;

wherein the portion-of-interest is determined based on the user selection.

5. The method of claim 1, wherein displaying the output comprises:

displaying, on the display, the plurality of segments of the physiological signal within the portion-of-interest and the potential abnormality as a function of time over the second period of time along a first axis and over the signal interval along a second axis; and graphically distinguishing, on the display, the potential abnormality from the plurality of segments of the physiological signal.

6. The method of claim 5, wherein the potential abnormality is graphically distinguished from the plurality of segments of the physiological signal by changing the color of the potential abnormality relative to the plurality of segments of the physiological signal.

7. The method of claim 1, wherein the initial representation of the physiological signal includes real-time measurements of the physiological signal.

8. The method of claim 1, wherein the initial representation of the physiological signal includes measurements of the physiological signal corresponding to at least one of the first period of time and the second period of time.

9. A method of automatically visually tracing a potential abnormality within a plurality of physiological signals, the method comprising:

receiving, via a plurality of sensors, the plurality of physiological signals from a subject, wherein the plurality of physiological signals are representative of a physiological parameter of the subject over a first period of time;

extracting, via at least one processor, a portion-of-interest of the plurality of physiological signals, wherein the portion-of-interest is representative of the physiological parameter of the subject over a second period of time, the second period of time being a subset of the first period of time;

determining, via the at least one processor, a signal interval for the portion-of-interest of the plurality of physiological signals;

for each of the plurality of physiological signals within the portion-of-interest, determining, via the at least one processor, a plurality of segments corresponding to at least one of the plurality of physiological signals based on the signal interval;

determining, via the at least one processor, a potential abnormality within the plurality of physiological signals based on the plurality of segments corresponding to each of the plurality of physiological signals;

generating, via the at least one processor, a plurality of three-dimensional visual outputs, wherein each output of the plurality of three-dimensional visual outputs corresponds to an individual physiological signal of the plurality of physiological signals, and wherein each output comprises the plurality of segments that correspond to each individual physiological signal and the potential abnormality as a function of time over the second period of time along a first axis and over the signal interval along a second axis; and displaying, on a display, two or more of the plurality of three-dimensional visual outputs, wherein the display includes an initial representation of one or more of the plurality of physiological signal, and the method further comprises:

on the display, automatically rearranging the initial representation to display both the initial representation and the generated two or more outputs.

10. The method of claim 9, wherein each physiological signal of the plurality of physiological signals corresponds to an individual sensor of the plurality of sensors.

11. The method of claim 9, wherein the physiological signal comprises electrical signals from the subject's heart, and the physiological parameter comprises heart beats.

12. The method of claim 11, wherein the potential abnormality includes at least one of the following: an ST elevation; an ST depression; a prolongation or shortening of the heart rate corrected QT interval; a prolongation or shortening of the QRS duration; a prolongation or shortening of the PR interval; an increased or decreased T-wave amplitude; and a change of P-wave or T-wave shape.

13. A system for visually tracing an abnormality within a physiological signal, the system comprising:

a plurality of sensors comprising electrodes and operatively connected to an external power supply;

a user interface comprising a display; and a processing unit operatively connected to the plurality of sensors and the user interface, wherein the processing unit comprises a memory and at least one processor, the memory storing instructions that, when executed by the at least one processor, perform the following:

receive, from the plurality of sensors, a physiological signal from a subject that is representative of a physiological parameter of the subject over a first period of time;

extract a portion-of-interest of the physiological signal that is representative of the physiological parameter of the subject over a second period of time, the second period of time being a subset of the first period of time;

determine a signal interval for the portion-of-interest of the physiological signal;

determine a plurality of segments of the physiological signal within the portion-of-interest based on the signal interval;

determine a potential abnormality within the physiological signal based on the plurality of segments of the physiological signal;

generate a three-dimensional visual output comprising the plurality of segments of the physiological signal within the portion-of-interest and the potential abnormality as a function of time over the second period of time along a first axis and over the signal interval along a second axis; and display, on the display of the user interface, the three-dimensional visual output, wherein the display includes an initial representation of one or more of the plurality of physiological signal, and the the processor is further configured to:

automatically rearranging the initial representation to display both the initial representation and the generated two or more outputs on the display.

* * * * *